United States Patent [19]

Oh et al.

[11] Patent Number: 4,834,096

[45] Date of Patent: May 30, 1989

[54] PLASTIC LIGATING CLIPS

[75] Inventors: Seik Oh; Ray McKinney, Jr., both of Raleigh, N.C.

[73] Assignee: Edward Weck Incorporated, Princeton, N.J.

[21] Appl. No.: 206,143

[22] Filed: Jun. 13, 1988

Related U.S. Application Data

[63] Continuation-in-part of Ser. No. 112,599, Oct. 26, 1987, abandoned.

[51] Int. Cl.⁴ .............................................. A61B 17/12
[52] U.S. Cl. .................................... 128/325; 128/346
[58] Field of Search ................ 128/325, 326, 327, 346

[56] References Cited

U.S. PATENT DOCUMENTS

| | | |
|---|---|---|
| 3,566,873 | 3/1971 | Melges . |
| 4,227,730 | 10/1980 | Alexander et al. . |
| 4,346,869 | 8/1982 | MacNeil . |
| 4,390,019 | 6/1983 | LeVeen et al. . |
| 4,418,694 | 12/1983 | Beroff et al. . |
| 4,605,002 | 8/1986 | Rebuffat . |
| 4,620,541 | 11/1986 | Gertzman et al. . |
| 4,638,804 | 1/1987 | Jewusiak . |
| 4,716,886 | 1/1988 | Schulman et al. . |
| 4,726,372 | 2/1988 | Perlin . |

Primary Examiner—John D. Yasko
Attorney, Agent, or Firm—Lawrence S. Levinson; Robert E. Lee, Jr.

[57] ABSTRACT

A polymeric, surgical clip having first and second curved leg members joined at their proximal end by a reduced thickness hinge portion and movable from an open position to a closed position for clamping a vessel between curved opposing inner surfaces which are substantially parallel when the clip is closed. The first leg member has a concave inner surface and a hook portion at its distal end curved toward the second leg member. A ligating clip applying instrument for applying the clip has a pair of handles pivoted about a hinge point and extends beyond the hinge point to form a pair of clip closing jaws equipped with means for engaging bosses located on the sides of the first and second leg members.

17 Claims, 5 Drawing Sheets

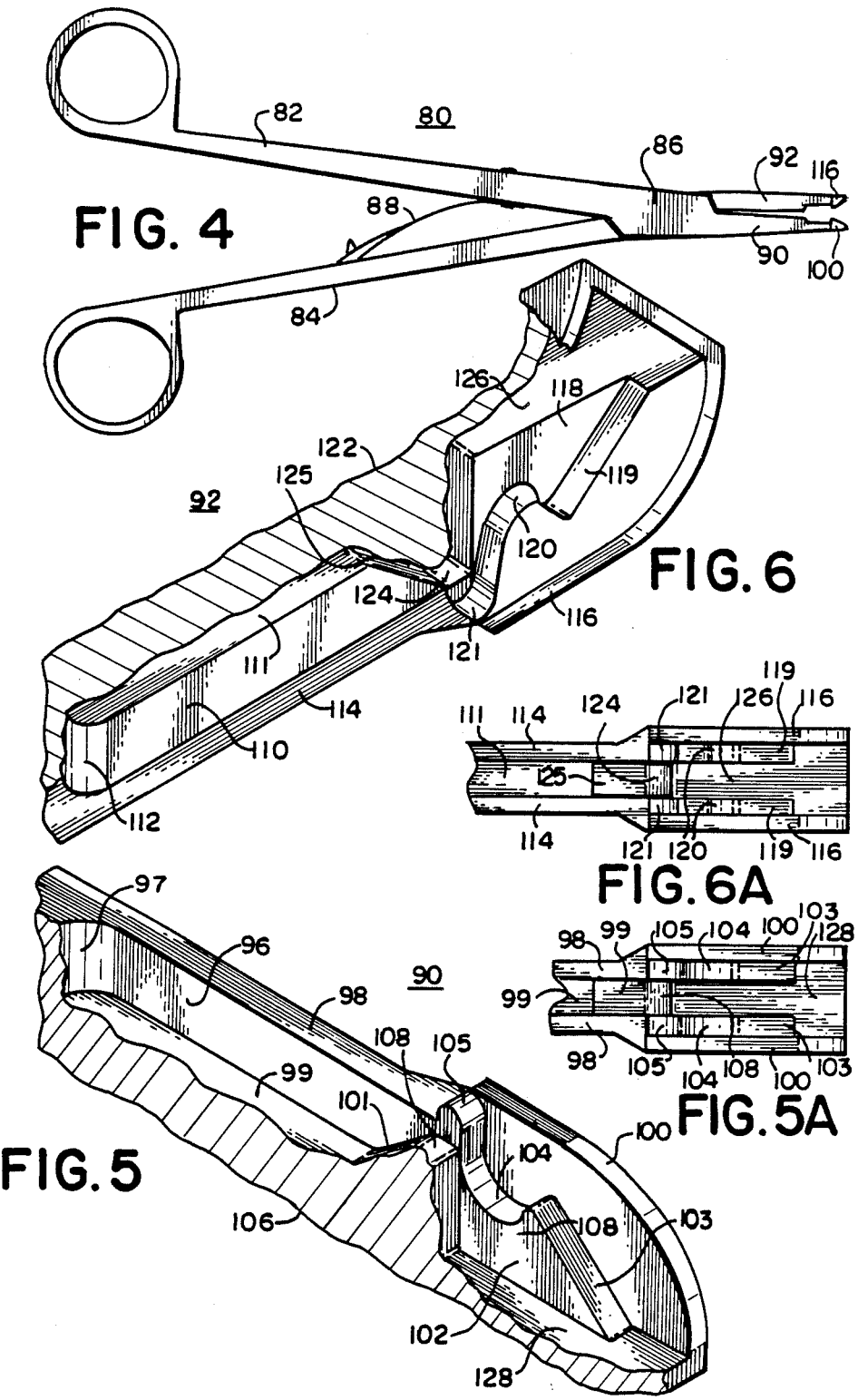

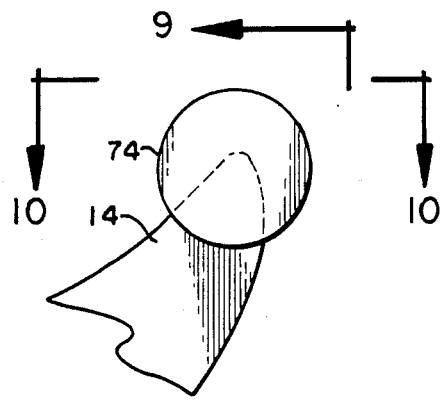
FIG.8
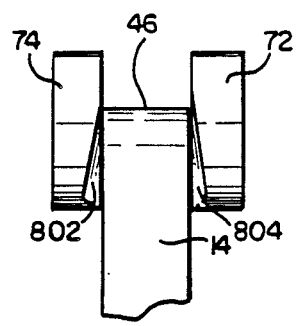
FIG.9
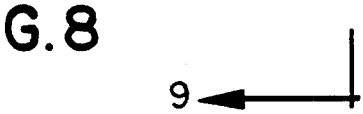
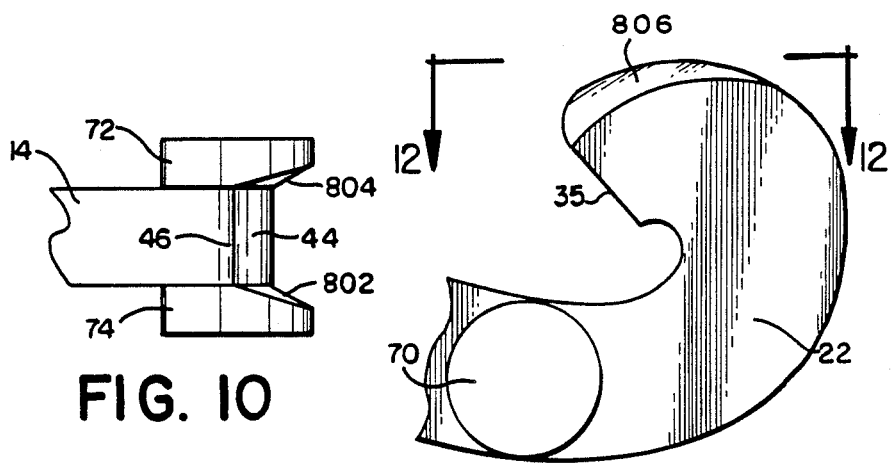
FIG. 10
FIG. 11
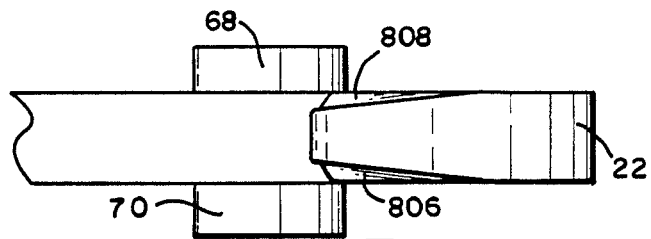
FIG. 12

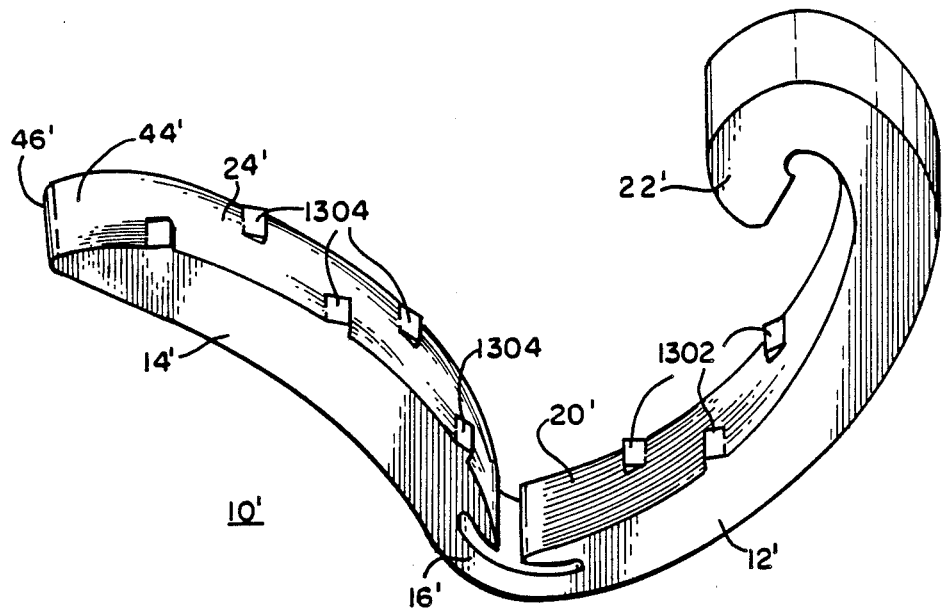
FIG. 13
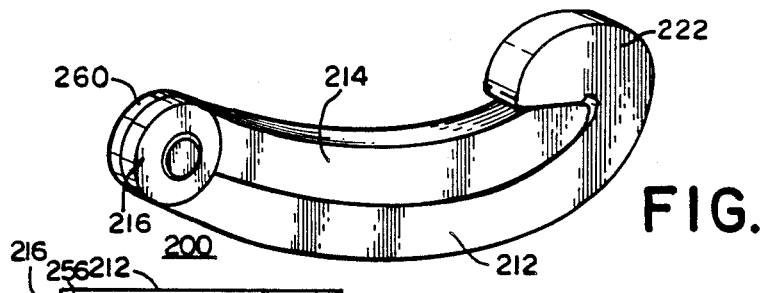
FIG. 14
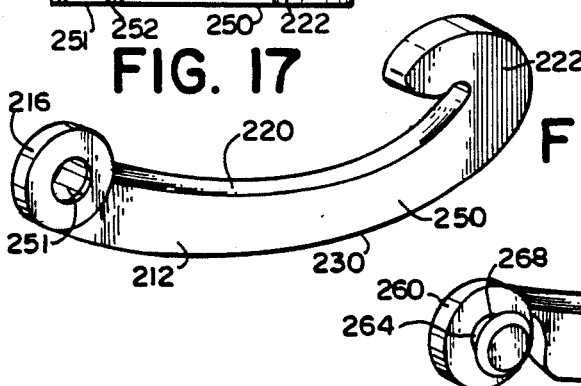
FIG. 17
FIG. 15
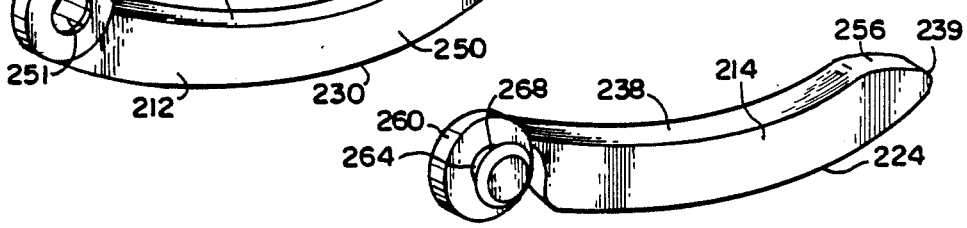
FIG. 16

PLASTIC LIGATING CLIPS

BACKGROUND OF THE INVENTION

This is a continuation-in-part of co-pending application Ser. No. 112,599 filed on Oct. 26, 1987 now abandoned.

The present invention relates to surgical clips and clip appliers and more particularly to polymeric hemostatic clips and instruments for applying them.

Surgical clips like hemostatic clips and aneurysm clips are often used in surgery to ligate vessels to stop the flow of blood. Surgical clips are also used to interrupt or occlude the oviduct or vas deferens in sterilization procedures. The clips are left in place permanently and within a period of time the ligated end of the vessel will close, that is, hemostasis or occlusion will occur.

Metal clips having generally U or V shapes have been used for years. The most common metals are alloys of tantalum, titanium or stainless steel, all of which are deformed into a closed position about the vessel and because of the nature of the metal stay deformed and resist any force by the vessel to expand or open up.

Metal clips cause a certain amount of interference with high technology diagnostic modalities, including Computer Tomography (CATSCAN) and Magnetic Resonance Imaging (MRI). In particular, the new and emerging MRI techniques place stringent demands on the non-interference properties of clips. For example, existing fast imaging techniques for MRI give rise to at least one order of magnitude in increased sensitivity to magnetic field inhomogenieties brought about by metallic clips Field uniformities of one in $10^5$ are required but metal clips, particularly stainless steel clips, can reduce the homogeniety in the locality of the clip to the order of $10^4$ or less.

To aggravate the situation even more recent developments in in vivo Magnetic Resonance Spectroscopy (MRS) create even greater demands on minimizing magnetic field interferences (field uniformities approximately one in $10^7$ required). Existing metal clips preclude the use of MRS data taken in the proximity of the metal clips. This region is as large as six clip diameters for titanium and tantalum and more than fifty clip diameters for stainless steel.

To overcome the above problems, in recent years plastic clips have been introduced. These clips generally should be as small as possible, e.g., as small as their metal counterparts. Plastic clips require a latching means to keep the clip closed once they are clamped about the vessel since, unlike metal clips, they have insufficient resistance to the forces tending to open the vessels.

Most of the new plastic clips now in the market are made of a biodegradable and absorbable polymeric material. Generally, the absorbable clips, owing to their comparatively high water sorption do not reflect the mechanical strength levels which are available from modern engineering plastics and therefore represent a size increase compromise in order to provide comparative strength. The use of high performance polymer materials permits increased design options for functional improvements.

It is, therefore, desirable to produce a small, but secure, biocompatible and strong polymeric surgical clip.

SUMMARY OF THE INVENTION

The surgical clip of the present invention is made of polymeric material and accordingly minimizes interference with high technology diagnostic modalities such as CATSCAN, MRI and MRS. At the same time, the clip is nearly as small as comparable metal clips, while maintaining sufficient strength and possessing high security in the clip's latching mechanism in the closed position. The clip is configured to provide a secure means of handling and application to avoid premature release from the applier.

A surgical clip is provided which comprises first and second curved leg members joined at their proximal ends by a hinge means and disposed to be latched together in the closed position at their distal ends. The leg members each include curved, opposing inner surfaces which are substantially parallel in the closed position, the inner surface of the first leg being concave in shape. The first leg member further includes a hook portion joined at its distal end and curved toward said second leg member. The hook portion is disposed to engage the outer surface of the end of the second leg member when the clip is in the closed position. The outer surface of the second leg member opposite the inner convex surface is concave in shape. This configuration provides a more secure latching mechanism, since any forces by the clamped vessel tending to open the clip will force the second leg to lengthen and the first leg member to shorten moving the distal end of the second leg member into further engagement with the hook portion. Because the thickness of the second leg member is smaller than it would have been without the concave outer surface, the second leg member will deflect upon clamping or in response to the forces exerted on it by the clamped vessel and because the thickness of each leg between its inner and opposite outer surfaces between the hinge and distal end is substantially equal to the thickness of the other leg, the total deflection necessary to accommodate closing and clamping of the vessel is distributed between the two legs helping to avoid breakage or failure of either leg. In the preferred embodiment, the radius of curvature of the inner concave surface of the first leg member is the same as the radius of curvature of the inner convex surface of the second leg member. This provides a constant compressive force across the entire width of the vessel being clamped.

The hinge means comprises a reduced thickness portion of the clip. The hinge means is formed by a continuous curve of large radius, with appropriate thickness which helps to reduce stress concentration in the hinge. The first and second leg members each further comprises a peninsular portion formed from an extension of the inner surface of the leg member. The peninsular portions extend substantially to the inner surface of the hinge means when the clip is in the closed position, preventing any portion of the clamped vessel from being located in the hinge region where total occlusion might be avoided.

In another embodiment of the hinge, the hinge comprises a curved slot which extends through the hinge from side to side positioned between the inner concave and outer convex curved surfaces of the hinge, preferably located closer to the concave surface than the convex surface. The slotted hinge increases flexibility of the hinge beyond that of a hinge with the same thickness, but not having the slot. The slot, however, is isolated from the vessel clamped between the leg inner surfaces by the interior concave surface of the hinge which avoids trapping of any portion of the vessel in the hinge region where failure to occlude the vessel would have been possible.

The inner and outer surfaces of the hook portion are substantially continuously curved to prevent excessive stress concentration occurring at corners or small radius points in the hook portion.

The clip further comprises means for allowing the clip to be engaged by a suitable forceps type applier comprising at least a pair of bosses located on the sides of the first leg member intermediate the hinge means and the hook portion and a pair of bosses also located on the sides of the second leg member at the distal end and so disposed as to extend beyond the end of the second leg member to provide two parallel and separately spaced surfaces which prevent lateral movement of the leg members relative to one another when the clip is closed. The bosses are used by the applier in holding and applying the clip.

The sides of the end of the hook portion are tapered to reduce the thicknesses of the outer surface of the end to provide alignment during the initial stages of clip closure.

The clip of the present invention may also include a plurality of protrusions on the inner surfaces of the leg members to aid in retention of the clamped vessel. The protrusions may be ratchet type, wedge shaped, to provide one way vascular movement into, but not out of, the clip.

A ligating clip applying instrument for applying two legged ligating clips having means for engaging the bosses located on the sides of the legs is also provided. The jaws of the instrument include a channel to receive the clip and a concave cut out near the end of each jaw in a wall on both sides of the channel. Each wall also includes an arcuate wall portion adjacent to and on the outside of the cut out.

The instrument further comprises a protrusion in the floor of each of said channels which is directed toward the opposite jaw, the protrusion being located proximally of the concave cut outs. Each protrusion engages a leg of the clip to assist in forcing the legs toward one another as the jaws are closed.

BRIEF DESCRIPTION OF THE DRAWINGS

FIGS. 2A through 2D are enlarged side elevational views of the clip and greatly enlarged portions of the clip.

FIG. 4 illustrates an enlarged planar elevational view of a forceps type applier useful with the clip of the present invention.

FIG. 5 is a greatly enlarged perspective view of a break away of a first jaw of the applier of FIG. 4.

FIG. 5A is a bottom planar view of the first jaw of FIG. 5.

FIG. 6 is a greatly enlarged perspective view of a break away of a second jaw of the applier of FIG. 4.

FIG. 6A is a bottom planar view of the second jaw of FIG. 6.

FIG. 8 is an enlarged side elevational view of an alternate embodiment distal end of a leg member of the clip of FIG. 1.

FIG. 9 is a front elevational view of the distal end of FIG. 8 taken along the lines and arrows 9—9 in FIG. 8.

FIG. 10 is a top view of the distal end of FIG. 8 taken along the lines and arrows 10—10 in FIG. 8.

FIG. 11 is a greatly enlarged side elevational view of an alternate embodiment hook portion of the clip of FIG. 1

FIG. 12 is a top view of the hook portion of FIG. 11 taken along the lines and arrows 12—12 in FIG. 11.

FIG. 13 is a greatly enlarged perspective view of a second alternate embodiment of the clip of FIG. 1.

FIG. 14 is a greatly enlarged perspective view of a third alternate embodiment of the clip of FIG. 1 shown in the closed position.

FIG. 15 is a perspective view of a first leg member of the clip of FIG. 14.

FIG. 16 is a perspective view of a second leg member of the clip of FIG. 14.

FIG. 17 is a reduced size elevational planar view in partial cross section of the first leg member of FIG. 15.

DETAILED DESCRIPTION OF THE DRAWINGS

Figure 1:
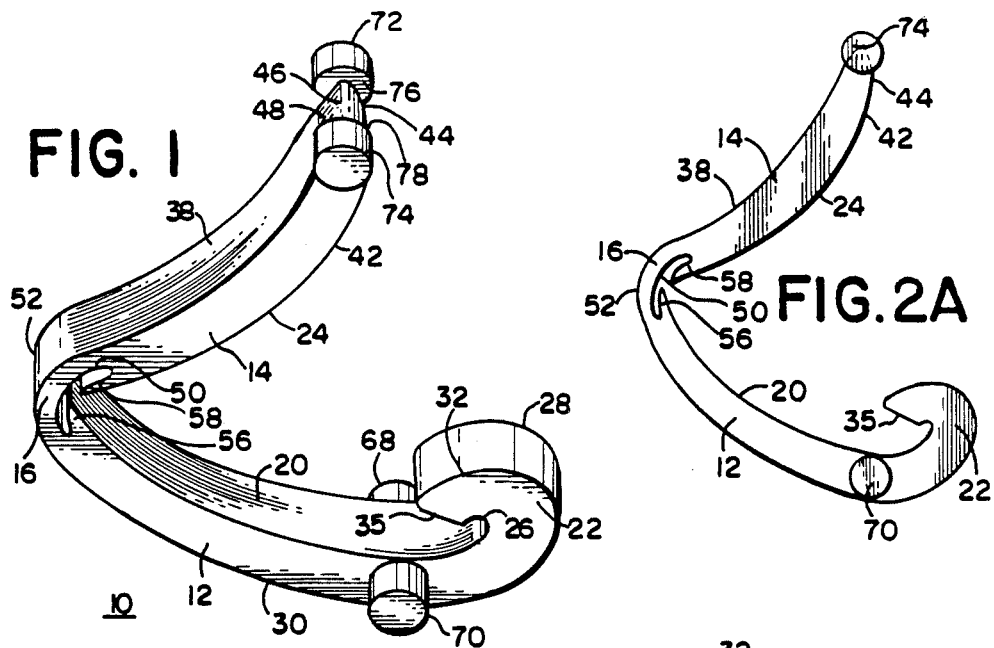
FIG. 1 is a greatly enlarged perspective view of the surgical clip of the present invention.
Figure 2B:
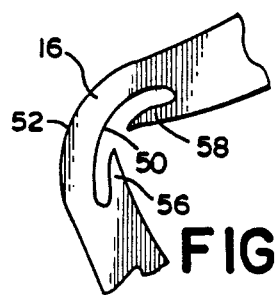
Figure 2C:
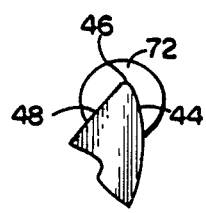
Figure 2D:
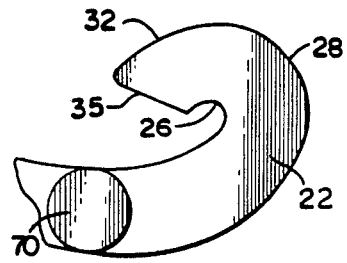

Referring now to FIGS. 1, 2A-2D and 3, a preferred embodiment surgical clip designated generally 10 is shown. It comprises a first curved leg member 12 and a second curved leg member 14 joined at their proximal ends by a hinge portion 16. First leg member 12 has a concave inner surface 20 and a curved hook portion 22 joined at its distal end. The inner surface 24 of second curved leg member 14 is convex and is adapted to be substantially parallel with concave inner surface 20 when the clip is closed, i.e; the radius of curvature of the concave inner surface 20 is substantially the same as inner convex surface 24. The hook portion 22 is curved toward the distal end of second leg member 14.

The inner and outer surfaces 26 and 28, respectively, of the hook portion 22 are continuously curved with the outer surface 28 continuing from the convex outer surface 30 of the first leg member with decreasing radius of curvature while the inner surface 26 continues from the inner concave surface 20 of the first leg member 12 in a decreasing radius of curvature to a constant terminal radius of curvature. In the preferred embodiment the thickness of the first leg member between its inner and outer surfaces 20 and 30, respectively, including the hook portion inner and outer surface 26 and 28, respectively, remains generally constant throughout its length.

The second leg member 14 has a banana like profile along its length between its inner convex surface 24 and outer concave surface 38. The thickness of the distal end has a rapid reduction in thickness because of the change in radius of curvature of its inner surface 24 at 42 to form a curved inner beveled surface 44 terminating in a tip 46 and the relatively flat beveled surface 48 joining the outer concave surface 38 to the tip 46.

The thickness of the second leg member 14 between its inner and outer surfaces 24 and 38, respectively, between the hinge portion 16 and its distal end may vary by ten to twenty percent with the leg being thickest at its center region. Generally the thickness of the second leg 14 is substantially the same as the thickness of the first leg 12 except for this variation in the center where the second leg may be slightly thicker. The thickness of the first leg 12 could be increased, however, in the center region to match the thickness of the first leg by varying the outer convex surface 30 of the first leg 12 but the radius of curvature of the concave inner surface 20 remains equal to the radius of curvature of the convex inner surface 24 of the second leg member 14. The thickness of the second leg member 14 being slightly thicker in the center causes the first leg member to deflect a little more than the second leg member when the clip is being clamped about a vessel, but the second leg member is disposed because of its outer concave surface to deflect substantially during closure so that total defection of the legs necessary to clamp a vessel and latch the clip is being shared about equally by the legs.

The hinge portion 16 has a substantially reduced thickness between its inner and outer surfaces 50 and 52, respectively, compared with the thicknesses of leg members 12 and 14. The outer surface 52 of the hinge portion 16 connects the outer surfaces 30 and 38 of the leg members 12 and 14, respectively, in a continuous curve. Leg members 12 and 14 include peninsular portions 56 and 58, respectively, which extend toward the inner surface 50 of the hinge portion 16. The peninsular portions are spaced apart from the proximal ends of the leg members coupled to the hinge portion and they are formed by an extension of the inner surfaces 20 and 24, respectively, of the leg members. The peninsular portions 56 and 58 extend substantially to the inner surface 50 of the hinge portion 16 to form the letter "C" shaped openings 60 and 62 when the clip is closed about the vessel. See FIG. 3.

Leg member 12 includes a pair of cylindrical bosses 68 and 70 coupled on opposite sides of leg member 12 intermediate the hook portion 22 and the hinge portion 16, but closer to the hook portion 22 in the preferred embodiment. The bosses extend laterally away from the leg member.

Leg member 14 includes a pair of cylindrical bosses 72 and 74 located at the tip 46 on opposite sides of the leg member 14 and extending laterally away therefrom. In the preferred embodiment, the coaxial center line of the bosses 72 and 74 passes through the tip portion of the leg member 14. See FIG. 2C where the boss 74 is removed showing the relationship of the tip 46 to the center of boss 72. The bosses 72 and 74 extend beyond the tip leaving spaced apart opposing surfaces 76 and 78, respectively.

FIG. 4 shows a forceps type clip applier 80 which includes two handles 82 and 84 coupled together and crossing at a hinge 86. The handles are biased into an open position by the spring 88. The handles 82 and 84 extend beyond the hinge 86 to form jaws 90 and 92, respectively.

FIG. 5 is an enlarged break away of a portion of the jaw 90 while FIG. 5A is a planar view of the jaw 90 of FIG. 5 both showing the details of its construction. The jaw 90 includes a channel 96 which extends from a position 97 rearward of the tip of the jaw towards the tip. The thickness of the outside walls 98 of the channel widen as they approach the end of the jaw to form arcuate outside walls 100 of the end of the jaw and inward adjacent walls 102 with rearwardly directed sloped surfaces 103 and concave cut outs 104. The inner surfaces of the walls 102 are contiguous with and in the same plane as the inner surfaces of the walls 98 which form the channel 96. Where the walls 98 widen to form the outside arcuate walls 100 and adjacent walls 102, the cut outs 104 extend beyond the top surfaces of the walls 98 toward the opposite jaw to form rounded shoulders 105. The adjacent arcuate walls 100 also are raised above the top surfaces of walls 98 by the same amount. The floor 99 of channel 96 is spaced apart and parallel with the top surfaces of walls 98 of the jaw along a portion extending from the rearward terminus 97 of the channel until the floor extends towards the opposite jaw along ramp 101 to form a protrusion 108 located just as the cut outs 104 extend above the top surfaces of walls 98. The protrusion 108 drops straight off to a flat portion 128 of the jaw which flat portion extends to the tip. The jaw has a flat outer bottom surface 106.

FIG. 6 is an enlarged break away of a portion of jaw 92 while FIG. 6A is a planar view of the jaw 92 of FIG. 6 both showing the details of its construction, which are identical to the construction of jaw 90. The jaw includes a channel 110 which extends from a position 112 rearward of the tip of the jaw toward the tip. The outside walls 114 of the channel widen as they approach the end of the jaw to form arcuate outside walls 116 of the end of the jaw and inward adjacent walls 118 with rearwardly directed sloped surfaces 119 and concave cut outs 120. The inner surfaces of the walls 118 are contiguous with and in the same plane as the inner surfaces of the walls 114 which form the channel 110. Where the walls 114 widen to form walls 116 and 118, the cut outs 120 extend towards the opposite jaw beyond the top surfaces of walls 114 to form rounded shoulders 121. The arcuate walls 116 extend beyond the top surface by the same amount. The floor 111 of channel 110 is spaced apart and parallel with the top surface of walls 114 of the jaw along a portion extending from the rearward terminus 112 of the channel until the floor extends towards the opposite jaw along ramp 125 to form a protrusion 124 located just as the cut outs 121 extend above the top surfaces of walls 114. The protrusion 124 drops straight off to a flat portion 126 of the jaw which extends to the tip. The jaw has a flat outer bottom surface 122.

FIGS. 7A through 7E show how the applier 80 is used in applying the clip 10. The clip 10 is in the open position with the general axes of the leg members forming an acute angle at the hinge, but the clip could be open as much as 90° or more. The jaws of the applier are biased open by an amount equal to the opening of the clip so that the flat surface 126 of jaw 92 and the flat surface 128 of jaw 90 slide over the bosses 72 and 74 of leg 14 and a portion of the outer surface 30 of leg 12 near the hook portion, respectively. As the applier is moved in the direction of arrow 700 in FIG. 7A, the bosses 72, 74 and 68, 70 are forced to ride up the rearwardly directed inclined surfaces 103 and 119 of walls 102 and 118, respectively, forcing the clip to close slightly until the bosses seat in cut outs 120 and 104 as in FIG. 7B.

The cut outs of each jaw are spaced apart from one another within the jaw by the channel of each jaw which is at least as wide as the width of the clip and the cut outs are disposed to receive the bosses. The concave cut outs keep the clips aligned and locked within the jaws during the closing. The concave cut outs 104 and 120 press against the bosses to begin closure of the clip.

Figure 7A:
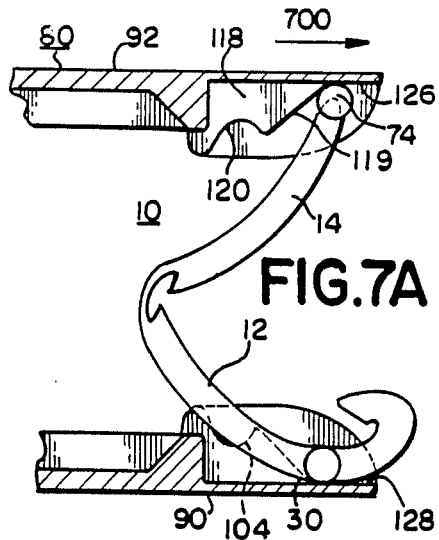
FIGS. 7A to 7E illustrate the use of the applier of FIGS. 4 to 6A in applying the clip of the present invention.
Figure 7B:
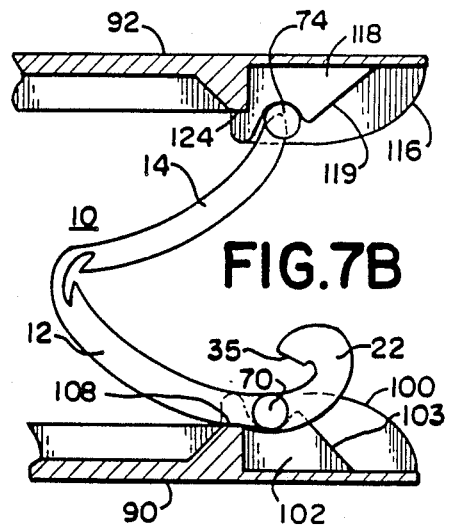
Figure 7C:
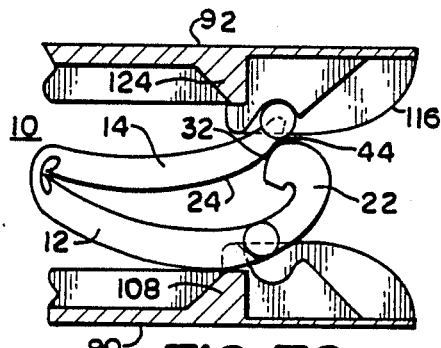
Figure 7D:
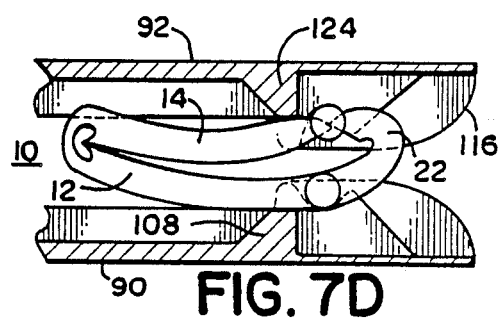
Figure 7E:
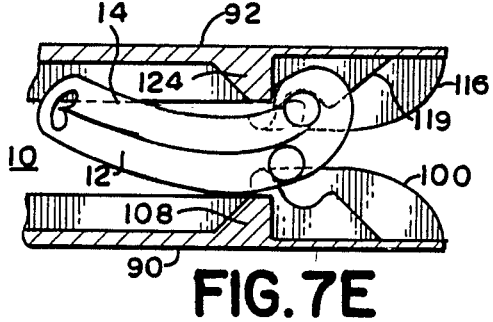

After the boss pairs 72, 74 and 68, 70 seat themselves in the concave cut outs, the raised shoulders 108 and 124 of jaws 90 and 92, respectively, press against the outside surfaces of leg members 12 and 14 to continue closure of the clip 10 (see FIGS. 7B–7E). Eventually the outside surface 32 of the hook portion 22 engages the inner surface 24 of leg member 14 near the curved bevel surface 44. See FIG. 7C. As the leg members continue to be pressed together, the rounded outside surface of the hook portion 22 slides along the curved bevel surface 44 and around tip 46 (FIG. 7D) until the flat surface 35 on the end of the hook portion 22 engages the flat beveled surface 48 on the outside of the leg member 14 closing the clip (FIG. 7E). The channels 96 and 110 accommodate the body of the clip within the jaws during the closing process. As best seen in FIG. 7D, both leg members deflect under the forces exerted on the clip during closure to accommodate movement of the hook portion of leg member 12 around the rounded tip of leg member 14.

Figure 3:
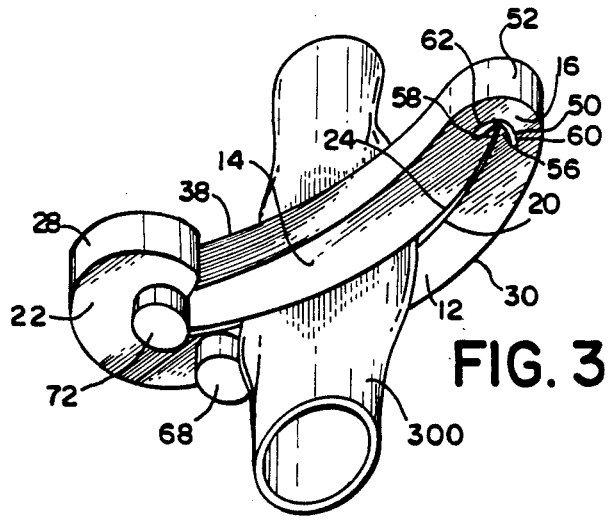
FIG. 3 shows the clip of FIG. 1 applied to a body vessel.

FIG. 3 shows the clip closed about a vessel 300. In the preferred embodiment the radius of curvature of the inner convex surface of second leg member 14 is substantially the same as the radius of curvature of the inner concave surface of first leg member 12. This causes a relatively even distribution across the width of the clamped vessel of the compressive forces being exerted by the clip leg members 12 and 14. The vessel 300, particularly if large or upon swelling, will exert a counter force against the legs of the clip after application tending to open up the clip. The outer concave surface reduces the thickness of the second leg member such that it will deflect and lengthen in response to forces by the clamped vessel tending to open the clip. Lengthening of the second leg member moves the distal end of the second leg member farther into the hook portion. At the same time, the forces by the clamped vessel exerted on the first leg member will tend to shorten the first leg member moving the hook portion closer to the hinge and the distal end of the second leg member. This configuration provides for a more secure latching. Also, because the thickness of the second leg member is smaller than it would have been without the concave outer surface, and is substantially the same as the first leg member between its inner and opposite outer surface, the total deflection necessary to accommodate closing and clamping of the vessel is distributed between the two legs with a substantial amount of deflection being taken up by second leg member helping to enhance the security of the latching effect and avoid premature failure of either leg. The thickness of the second leg member in the center region is slightly larger than the thickness of the first leg member or corresponding center region in order that the second leg member will bend slightly less than the first leg member to avoid passing the flattening position from which unlatching is facilitated. Both leg members can be made with equal thickness, however.

Since the objective of the clip is to occlude or seal off the vessel, it is imperative that the entire vessel be occluded. In some clips it is possible that a portion of the vessel becomes trapped in a void adjacent the inner surface of the hinge portion and is not occluded by the clip leg members. Such an occurrence would allow blood or fluid to pass through the unoccluded portion of the vessel. To avoid this on the clip of the present invention, each leg member comprises a peninsular portion (56 and 58) which is formed by an extension of the inner surface of each leg member and which substantially extends back to the inner wall 50 of the hinge when the clip is closed. The only void left in the hinge region are the "C" shaped voids 60 and 62 which are on opposite sides of the peninsular portions from the vessel clamping inner surfaces of the leg members. The peninsular portions are formed spaced apart from the leg member portions coupled to the hinge portion to avoid the resistance to closing which would be created by compressing the leg members in the region of the hinge upon closing. Yet the narrowed hinge is still strong because of the continuous curve formed by its inner and outer surfaces, and no void is accessible to trap the clamped vessel.

Figure 18:
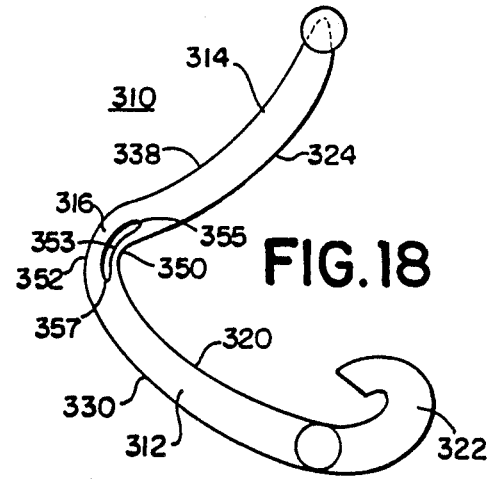
FIG. 18 is a greatly enlarged side elevational view of a fourth alternate embodiment of the clip of FIG. 1.

With reference to the hinge portion, FIG. 18 shows an alternate embodiment clip 310 which is identical to the clip 10 in FIGS. 1 through 3 except for the hinge portion 316. The clip 310 comprises curved first and second leg members 312 and 314 joined at their proximal ends by hinge portion 316. First leg member 312 has a concave inner surface 320 and curved hook portion 322 joined at its distal end. The inner surface 324 of second curved leg member 314 is convex and is adapted to be substantially parallel with concave inner surface 320 When the clip is closed, i.e., the radius of curvature of the convex surface 324 is substantially the same as the radius of curvature of the concave surface 320. The outer surface 338 of the second leg member 314 is concave between the hinge portion and its distal end. Hinge portion 316 comprises an inner continuously curved concave surface 350 which joins the inner concave and convex surfaces 320 and 324, respectively, and an outer continuously curved surface 352 which joins outer convex and concave surfaces 330 and 338, respectively, and which is spaced apart from inner hinge concave surface 350. The hinge portion 316 further includes a curved slot 353 which is located between curved hinge surfaces 350 and 352, being positioned closer to concave hinge surface 350 than to convex hinge surface 352. The slot extends completely through the hinge portion 316 from side to side and its opposite ends 355 and 357 extend into the proximal ends of the leg members 312 and 314, respectively. The slot 353 provides added flexibility to the hinge 316 but the inner concave surface 350 prevents any portion of the clamped vessel from being trapped within the slot 353.

The inner surfaces of the side bosses 72 and 74 which extend beyond the tip 46 of the leg member 14 prevent the hook member and leg member 14 from moving laterally relative to one another, once the clip is closed.

By providing a continuous relatively large radii of curvature to both the inner and outer surfaces of the hinge portion and the hook portion, sharp interior corners which create unwanted stress concentration, which can lead to clip failure, are eliminated.

FIGS. 8 through 12 show modifications to the clip which provide a means for guiding the clip into locking engagement. The inside opposing surfaces of the side bosses 72 and 74 at the tip of leg member 14 are provided with an outward taper 802 and 804, each of which extends away from the side of the second leg member and increases until the circumference of the boss is reached. The taper is present at the curved beveled surface 44 and decreases as the tip 46 is approached.

The end of the hook portion 22 is tapered at 806 and 808 to narrow the outer surface as it approaches the flat 35 on the hook portion. See FIGS. 11 and 12. As the narrowed outer surface of the end of the hook portion slides along the curved beveled surface 44 it is received by the enlarged opening between the opposing surfaces of the lateral bosses 72 and 74 created by the tapers 802 and 804 thereon. As the hook portion continues to slide between the lateral bosses the opening due to the tapers on the bosses 72 and 74 narrows aligning the first leg member 12 with the second leg member 14.

FIG. 13 is an alternate embodiment of the clip of FIGS. 1-3. The clip 10' of FIG. 13 further includes a plurality of protrusions 1302 on the inner surface 20' of the leg member 12', while leg member 14' includes a plurality of protrusions 1304 on its inner surface 24'. The protrusions are wedge shaped with the wedge opening up towards the hinge portion. The protrusions engage the tissue of the vessel being clamped and assist in preventing the vessel sliding laterally or longitudinally during or following clip closure. It is preferable that the clip clamp the vessel substantially across the vessel at 90° to the axis of the vessel. The vessel being dynamic may move or pulse and such movement may cause the clip to become misaligned degrading its performance or function. The protrusions help in preventing this.

The clip of FIGS. 1-13 is preferably a single integral piece of molded plastic. The plastic material chosen is preferably one of the many relatively strong engineering plastics available today which are commonly used in surgical implant operations and are biocompatible. Two examples of suitable plastics are polyethylene terephthalate (PET) and polyoxymethylene. These are both thermoplastic materials that can be injection molded, extruded or otherwise thermally processed into shaped articles and filaments. An alternate, molding grade polyester, polybutylene terephthalate (PBT) can also be used.

As mentioned earlier it is preferable that any plastic surgical clip, such as a hemostatic clip, be as small as its metal equivalent. The preferred embodiment clip can be made as small as seven millimeters in overall length in the closed position as measured from the back of the hinge to the outside of the hook portion. This is to be compared with a medium size metal hemostatic clip which is approximately six millimeters in length when closed. Each leg of the polymeric clip of the present invention has a maximum thickness in the order of 1.0 millimeters or less with a weight of about 0.015 grams, a volume of 0.01 cubic centimeters and an opening of 4 millimeters or more.

In the preferred embodiment, the radius of curvature of the inner surface of the leg 12 starts out as 0.166 inches near the peninsular portion 56, changes to 0.222 inches at the center region up to the hook portion 22 where it changes to 0.052 inches and then to 0.007 inches. The outer surface of the hook portion starting at its end 32 is 0.045 inches then 0.036 inches. As the hook portion ends and the outer surface 30 of leg member 12 continues towards the hinge the radius of curvature changes from 0.108 inches, to 0.246 inches, to 0.171 inches near the hinge 16. The hinge's outer surface 52 has a radius of 0.042 inches until the outer concave surface 38 of the leg member 14 begins at the radius of 0.161 inches and then 0.231 inches near the tip 46 (radius of 0.003 inches). The radius of the curved beveled surface 44 is 0.044 inches up until the start of the convex inner surface 24 of leg member 14 which is 0.222 inches and then 0.166 inches. The radii are provided to give an example of the degree of curvature of the clip and to show that the curved surfaces are generally continuous. The centers of the radii, even for the concave and convex surfaces, such as, the inner and outer surfaces of the leg members, are not generally the same. While these radii reflect the radii for the preferred embodiment clip, it should be understood that variations or changes from these radii are encompassed by the present invention curved clip.

Referring now to FIGS. 14 through 17, an alternate embodiment polymeric clip 200 made from two pieces is shown. The clip comprises a first leg member 212 with inner concave curved surface 220 and outer convex curved surface 230. The leg member comprise a hook portion 222 integrally formed at its distal end similar in function and shape to the hook portion 22 of clip 10. It further comprises a cylindrical socket portion 216 integrally formed at its proximal end. The cylindrical socket portion is approximately one half the thickness of the first leg member 212 as measured along the axis of the socket from one side of the leg member 212 to its opposite side. A first side of the cylindrical socket portion is in the same plane as the outer side 250 of the first leg member. The opening 251 through the socket 216 first becomes larger from this side for a distance along the axis of the socket until it abruptly narrows forming an interior annular ledge 252. The opening maintains a constant diameter for a distance at 254 when for a short distance it becomes larger and opens up at the opposite side 256 of the socket.

Leg member 214 includes and inner convex surface 224 and an outer concave surface 238. The outer concave surface is joined with the tip 239 of the distal end of the leg 214 by a flat beveled surface 256. At the proximal end the leg member 214 includes an integrally formed enlarged cylinder 260 whose thickness along its axis is about one half the thickness of the leg member 214. The outside end surface of the cylinder is flush with or in the same plane as the outside surface 262 of the leg member 214. Integrally formed with the enlarged cylinder 260 is a smaller diameter cylinder 264, coaxial with cylinder 260 and extending away therefrom along the common axis. The end of the smaller cylinder 264 has a trapezoidal shape which forms an annular ledge 268 spaced apart from the end of the smaller cylinder.

The cylindrical socket 216 of the first leg member 212 is adapted to receive the smaller diameter cylinder 264 in a snap like fit. When the end of the smaller cylinder is pressed into the enlarged opening of the socket in the side 256 of leg 212, the smaller cylinder passes through the socket with the ledge 268 of the end of the smaller cylinder compressed within the constant diameter portion 254 of the socket until the end passes the interior ledge 252. At that point the end of the smaller cylinder snaps into place with the region of the socket formed by ledge 252 adapted to receive the trapezoidal portion of the smaller diameter cylinder 264. The ledge 252 engages the ledge 268 preventing the legs from being separated once they are snapped together. The completely circular, enlarged hinge formed by the structure just described provides a very strong hinge to withstand hinge failure particularly during application of the clip to a vessel.

While the embodiments of the surgical clip described herein above are particularly adapted for hemostatic application, they may also have other applications, e.g. as oviduct or vas deferens clips.

What is claimed is:

1. A polymeric surgical clip comprising first and second curved leg members joined at their proximal ends by a resilient hinge means, each leg member having a vessel clamping inner surface and an opposite outer surface, said vessel clamping inner surface being in opposition to the vessel clamping inner surface of the other leg member, said first leg member terminating at its distal end in a deflectable hook member curved toward said second leg member, said second leg member terminating at its distal end is a complimentary locking portion to said hook member whereby when said first and second leg members are moved from an open position to a closed position about said hinge means, the hook member deflects about the distal end of said second leg member to lock the clip in a closed position, the inner surface of the first leg member having a concave radius of curvature between the hinge means and the hook member, the inner surface of the second leg member having a convex radius of curvature between the hinge means and its distal end and the outer surface of said second leg member having a concave radius of curvature between the hinge means and its distal end.

2. The clip of claim 1 wherein the outer surface of said first leg member has a convex radius of curvature.

3. The clip of claim 2 wherein the thickness of said first leg member between said inner and outer surfaces between the hinge portion and the hook member is substantially the same as the thickness of said second leg member between said inner and outer surfaces between the hinge portion and its distal end.

4. The clip of claims 1, 2 and 3 wherein the radius of curvature of said inner concave surface of said first leg member is substantially equal to the radius of curvature of said inner convex surface of said second leg member.

5. The surgical clip of claim 1 wherein said hinge means comprises a portion of said clip which has a reduced thickness compared to the thickness of said first and second leg members and whose outer surface forms a continuous curve with the outer surfaces of said first and second leg members at said hinge means.

6. The surgical clip of claim 5 wherein said first and second leg members each comprises a peninsular portion spaced apart from the hinge means where the leg member is coupled to the hinge means and formed from an extension of the interior surface of the leg member which interior surface extends substantially to the inner surface of the hinge means when said clip is in the closed position.

7. The surgical clip of claim 1 wherein said hinge means comprises a portion of said clip having an outer curved surface which forms a continuous curve with the outer surfaces of said first and second leg members and an inner curved surface spaced apart from the hinge means outer surface, said hinge means inner curved surface forming a continuous curve with the inner surfaces of said first and second leg members free of any interior corners in said hook means.

8. The clip of claim 7 wherein said hinge means comprises a curved slot between said hinge means inner and outer curved surfaces, the outer surface of said slot being concave to said slot and the inner surface of said slot being convex to said slot.

9. The clip of claim 8 wherein said slot is closer to said hinge means inner concave surface than said hinge means outer convex surface.

10. The surgical clip of claim 1 wherein said clip comprises means coupled to said first and second leg members for engagement with a suitable clip applier for applying said clips.

11. The surgical clip of claim 10 wherein said engagement means comprises a pair of bosses joined to opposite sides of said first leg member intermediate said hinge means and said hook portion, and a pair of bosses joined to opposite sides of said second leg member at the distal end of said second leg member, said opposite sides of said first and second leg members extending between said leg member inner and outer surfaces.

12. The surgical clip of claim 11 wherein a portion of said pair of bosses joined to said second leg member extend longitudinally beyond the distal end to form substantially parallel and spaced apart surfaces which prevent lateral movement of said first and second leg members relative to one another when the clip is in the closed position.

13. The clip of claim 12 wherein the sides of the end of the hook portion are tapered towards one another to reduce the thickness of the hook portion and the inner surfaces of the bosses on said second leg member in the extended portion are tapered away from the second leg to receive the tapered portion of the hook portion to guide the clip into the closed position.

14. The clip of claim 1 wherein the inner surfaces of said clip each comprise a plurality of protrusions for providing improved vessel retention during closure of the clips.

15. The clip of claim 12 where each of said protrusions is a wedge shaped opening toward said hinge means.

16. The clip of claim 1 wherein said hinge means is integrally formed with said first and second leg members and said hook portion is integrally formed with said first leg member.

17. The clip of claim 1 wherein said clip comprises a cylindrically shaped socket integrally formed within the proximal end of said first leg member and a protruding cylinder integrally formed on the proximal end of said second leg member, said socket adapted to receive said protruding cylinder in a snap on fit.

* * * * *